United States Patent [19]

Evans

[11] Patent Number: 5,696,281

[45] Date of Patent: Dec. 9, 1997

[54] LIQUID PHENOLIC ANTIOXIDANTS

[75] Inventor: Samuel Evans, Marly, Switzerland

[73] Assignee: Ciba Specialty Chemicals Corporation, Tarrytown, N.Y.

[21] Appl. No.: 454,362

[22] PCT Filed: Dec. 10, 1993

[86] PCT No.: PCT/EP93/03502

§ 371 Date: Jun. 20, 1995

§ 102(e) Date: Jun. 20, 1995

[87] PCT Pub. No.: WO94/14748

PCT Pub. Date: Jul. 7, 1994

[30] Foreign Application Priority Data

Dec. 21, 1992 [CH] Switzerland ................. 3905/92

[51] Int. Cl.⁶ .................................................. C07C 69/76
[52] U.S. Cl. ............................................................ 560/75
[58] Field of Search ............................................. 560/75

[56] References Cited

U.S. PATENT DOCUMENTS

| | | | |
|---|---|---|---|
| 3,247,240 | 4/1966 | Meier et al. | 260/473 |
| 4,032,562 | 6/1977 | Dexter et al. | 260/473 |
| 4,228,297 | 10/1980 | Haeberli et al. | 560/75 |
| 4,477,638 | 10/1984 | Reid | 526/84 |
| 4,713,475 | 12/1987 | Spivack et al. | 560/75 |

FOREIGN PATENT DOCUMENTS 1290848  9/1972  United Kingdom .

OTHER PUBLICATIONS

Chem. Abstract 63:13506b.

Chem. Abstract 62:2887b.

*Primary Examiner*—Paul J. Killos
*Attorney, Agent, or Firm*—Michele A. Kovaleski; Luther A. R. Hall; Victoria M. Malia

[57]  ABSTRACT

The present invention relates to novel liquid phenolic antioxidants, to organic materials stabilized with said compounds against thermal, oxidative and/or actinic degradation, and to the use of said novel compounds as stabilizers.

16 Claims, No Drawings

LIQUID PHENOLIC ANTIOXIDANTS

This application is a 371 of PCT/EP93/03502 Dec. 10, 1993.

Sterically hindered phenols are known stabilisers for organic materials that are susceptible to thermal, oxidative and/or actinic degradation. Thus, for example, U.S. Pat. No. 4,032,562 discloses phenol stabilisers that may contain up to 3 to 8 alkylene oxide units and are terminated with —OH, methoxy or ethoxy. U.S. Pat. No. 4,713,475 and U.S. Pat. No. 4,228,297 disclose phenol-substituted propionates containing 3 to 50 carbon atoms in the ester radicals. U.S. Pat. No. 4,477,638 teaches the use of different phenol-substituted propionic acid derivatives as chain-terminators for the synthesis of polyvinyl chloride. BE patent 645 505 discloses stearyl 3-(3,5-di-tert-butyl-4-hydroxyphenyl)propionate as component of a stabiliser mixture together with phosphites and thioesters. Analogous compounds are disclosed in BE patent 636 254 and GB 1 290 848 the compound being used in the Belgian patent as component of a stabiliser mixture together with a selection of many other components. U.S. Pat. No. 3,247,240 discloses a process for the preparation of carbonyl compounds that contain hindered phenol groups.

Some novel phenolic carboxylic acid esters have now been found that have particularly good stabiliser properties.

Specifically, the invention relates to compounds of formula I

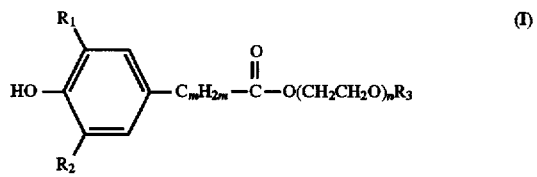

wherein
$R_1$ is $C_1$–$C_{18}$alkyl, $C_5$–$C_{12}$cycloalkyl, phenyl, benzyl, α-methylbenzyl or α,α-dimethylbenzyl,
$R_2$ is hydrogen or has one of the meanings given for $R_1$,
$R_3$ is $C_4$–$C_{50}$alkyl,
m is 1, 2 or 3, and
n is a number from 1 to 15.

$R_1$ and $R_2$ defined as $C_1$–$C_{18}$alkyl are a branched or unbranched radical. Branched $C_1$–$C_{18}$alkyl will be understood as meaning radicals containing secondary carbon atoms as well as those containing tertiary carbon atoms. Typical examples of branched and unbranched $C_1$–$C_{18}$alkyl radicals are methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl, preferably methyl, ethyl, propyl, isopropyl, n-butyl, sec-butyl, isobutyl, tert-butyl. Methyl and tert-butyl are particularly preferred.

$R_1$ and $R$ defined as $C_5$–$C_{12}$cycloalkyl are cyclopentyl, cyclohexyl, cycloheptyl, cyclooctyl, cyclononyl, cyclodecyl, cycloundecyl or cyclododecyl. Cyclopentyl and cyclohexyl are preferred. Cyclohexyl is particularly preferred.

$R_3$ defined as $C_4$–$C_{50}$alkyl is a branched or linear radical. Branched $C_4$–$C_{50}$alkyl will be understood as meaning radicals containing secondary carbon atoms as well as those containing tertiary carbon atoms. Typical examples of branched and unbranched $C_4$–$C_{50}$alkyl radicals are n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl, docosyl, tetracosyl, pentacosyl, octacosyl, triacontyl, dotriacontyl, tetracontyl or pentacontyl.

$R_3$ is preferably unbranched alkyl, more particularly nonyl, decyl, undecyl, dodecyl, tridecyl, tetradecyl and pentadecyl. $R_3$ is typically $C_8$–$C_{40}$alkyl, conveniently $C_{10}$–$C_{40}$alkyl or $C_{10}$–$C_{18}$alkyl, preferably $C_{12}$–$C_{18}$alkyl.

$C_mH_{2m}$ is linear or branched alkyl containing not more than 3 carbon atoms and is typically methylene, ethylene, propylene, ethylidene or propylidene, preferably methylene and ethylene. Ethylene is most preferred.

The compounds of formula I are typically prepared by transesterifying phenol esters of formula II with alcohols of formula III in the presence of a catalyst:

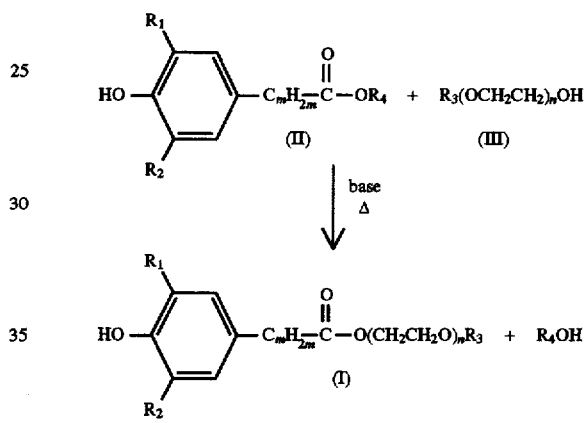

$R_1$, $R_2$, $R_3$, n and m are as defined for formula I, $R_4$ is an alkyl radical, preferably methyl or ethyl.

Those skilled in the art will be familiar with such reactions, which are described, inter alia, in standard textbooks of chemistry or also in U.S. Pat. Nos. 4,228,297, 3,644,482 and 3,285,855. The reaction can be carried out in per se known manner, conveniently by adding one of the two educts to the second educt and throughly mixing both reactants, preferably excluding atmospheric oxygen. The reaction can be carried out in the presence of a solvent, typically toluene, or also without a solvent. The reaction temperatures depend on the respective educts and are in the range from 50°–200° C., preferably from 60°–80° C. and, most preferably, from 80°–170° C. During the transesterification, it is expedient to add customary transesterification catalysts to the reaction mixture. Exemplary of such catalysts are organic or inorganic bases such as lithium amide, lithium methoxide or potassium hydroxide, or Lewis acids such as dibutyltin oxide.

The transesterification reactions are usually equilibrium reactions. To shift the equilibrium to the product side it is therefore expedient to remove continuously a component that forms from the reaction mixture, conveniently by distillative removal of the alcohol. Another means of shifting the equilibrium consists in increasing the concentration of one or both reactants, preferably that of the alcohol.

The resultant product can likewise be isolated and purified by known methods, typically by washing with water, extraction with an organic solvent, distillation and/or chromatography. The preferred solvent for the extraction and for the extraction and for the chromatographic purification step is hexane, ethyl acetate or a mixture thereof.

Other preparative methods are typically the esterification of phenolic carboxylic acids or carbonyl chlorides with alcohols. The estefification of the phenolic carboxylic acids is acid-catalysed. It is expedient to carry out this reaction using a water separator, removing water by distillation and/or using reagents that take up water of reaction, typically dicyclohexyl carbodiimide. When esterifying carbonyl chlorides, it is convenient to add an acid acceptor to the reaction mixture. Suitable acid acceptors are typically amines such as pyridine or triethylamine, or bases such as sodium hydroxide. The amount of acid acceptor is preferably at least equivalent to the amount of the acid chloride and is conveniently 1 to 2 equivalents, based on the acid chloride.

Those skilled in the art will be familar with the above described reactions, which are described in standard textbooks of chemistry.

The educts for preparing compounds of formula I are widely commercially available and those skilled in the art will be familiar with their preparation. They are fully described in the chemical literature.

Alcohols are used in all of the above described syntheses of compounds of formula I. Such alcohols are also commercially available in the form of mixtures of compounds having a different number of carbon atoms (in accordance with $R_3$) and a different number of ethylene oxide units (in accordance with n) (e.g different ®Dobanols sold by SHELL). The preparation of compounds of formula I with such mixtures is of particular interest.

The pure compounds can be obtained by conventional separating methods such as distillation or chromatography. The direct use of resultant mixtures of compounds of formula I as antioxidants is, however, of especial interest.

The invention therefore also relates to mixtures of compounds of formula I obtainable by reacting of compounds of formula IV

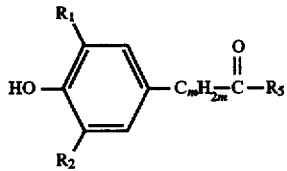

(IV)

wherein
$R_1$ is $C_1$–$C_{18}$alkyl, $C_5$–$C_{12}$cycloalkyl, phenyl, benzyl, α-methylbenzyl or α,α-dimethylbenzyl,
$R_2$ is hydrogen or has one of the meanings given for $R_1$, m is 1, 2 or 3, and
$R_5$ is OH, $C_1$14 $C_4$alkoxy or Cl,
with mixtures of alcohols of formula III

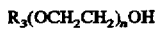

(III)

wherein
$R_3$ is $C_4$–$C_{50}$alkyl, and
n is a number from 1–15, said mixture of alcohols comprising at least two alcohols having different values for n and/or containing different radicals $R_3$.

Mixtures of alcohols comprising 2–6, preferably 4–6 and, most preferably, 4 different alcohols will typically be used.

The alcohols may be present in the mixtures in different ratios. For example, the ratio of two alcohols containing different radicals $R_3$ or having different values for n may be 1:99 to 99:1. When using a mixture of alcohols in which typically $A=HO$—$(CH_2CH_2O)_5$—$C_2H_{25}$, $B=HO$—$(CH_2CH_2O)_5$—$C_{13}H_{27}$, $C=HO$—$(CH_2CH_2O)_6$—$C_{12}H_{25}$ and $D=HO$—$(CH_2CH_2O)_6$—$C_{13}H_{27}$, the amounts of components A, B, C and D may each be from 1–97%, the sum of the components being 100%.

Preferred compounds of formula I are those wherein $R_1$ is $C_1$–$C_4$alkyl or cyclohexyl, preferably tert-butyl.

Further interesting compounds of formula I are those wherein $R_3$ is $C_8$–$C_{30}$alkyl, preferably $C_{10}$–$C_{18}$alkyl.

Compounds of formula I, wherein m is 2 or 3, preferably 2, merit special interest.

Those compounds of formula I, wherein n is 2–12, preferably 3–8, are especially preferred.

Interesting compounds of formula I are those wherein $R_1$ and $R_2$ are identical.

Other preferred compounds of formula I are those wherein $R_1$ and $R_2$ are tert-butyl, $R_3$ is $C_{10}$–$C_{18}$alkyl, n is 3–8 and m is 2.

Preferred mixtures of compounds of formula I are those wherein $R_3$ is nonyl, decyl and undecyl.

Further preferred mixtures of compounds of formula I are those wherein $R_3$ is dodecyl and tridecyl.

To be singled out for special mention are also mixtures of compounds of formula I, wherein $R_3$ is dodecyl, tridecyl, tetradecyl and pentadecyl.

Further interesting mixtures contain compounds of formula I wherein $R_3$ is tetradecyl and pentadecyl.

Mixtures of compounds of formula I, wherein n is 2 and 5 or 5 and 6, are also of particular interest.

The compounds of formula I and the mixtures thereof are suitable for stabilising organic materials against thermal, oxidative and actinic degradation. Particular attention is drawn to their outstanding action as antioxidants for stabilising organic materials.

Illustrative examples of such materials are:
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisafion using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst stystems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrerie and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyarnide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.

The suitable lubricants and hydraulic fluids may be based on mineral or synthetic oils or mixtures thereof. The lubricants are known to the skilled person and described in the pertinent technical literature, for example in Dieter Klamann, "Schmierstoffe und verwandte Produkte" (Lubricants and Related Products), Verlag Chemie, Weinheim, 1982, in Schewe-Kobek, "Das Schmiermittel-Taschenbuch" (The Lubricant Handbook), Dr. Alfred H üthig-Verlag, Heidelberg, 1974) and in "Ullmanns Enzyklop ädie der technischen Chemie", (Encyclopedia of Industrial Chemistry), Vol. 13, pages 85–94 (Verlag Chemie, Weinheim, 1977).

Further objects of the invention are compositions comprising an organic material that is susceptible to oxidative, thermal and/or actinic degradation and at least one compound of formula I, as well as the use of compounds of formula I for stabilising organic material against oxidative, thermal and/or actinic degradation.

The invention therefore further relates to a process for stabilising organic materials against oxidative, thermal or light-induced degradation, which comprises incorporating therein at least one compound of formula I.

Those compositions comprising an organic material that is susceptible to oxidative, thermal and/or actinic degradation and a mixture of compounds of formula I, as well as the use of mixtures of compounds of formula I for stabilising organic material against oxidative, thermal and/or actinic degradation, have a particularly interesting utility.

Furthermore, the invention relates to a method of stabilising organic materials against oxidative, thermal or light-induced degradation, which comprises incorporating therein a mixture of compounds of formula I.

The use of compounds of formula I as antioxidants for synthetic organic polymers is of particular interest.

Preferred organic materials are polymers, typically synthetic polymers, preferably thermoplastic polymers. Especially preferred organic materials are polyolefins and styrene copolymers, for example those listed under items 1 to 3 above and under items 5 and 6 above, preferably polyethylene and propylene as well as ABS and styrene-butadiene copolymers. The invention therefore preferably relates to compositions in which the organic material is a synthetic organic polymer or a mixture of such polymers, in particular a polyolefin or a styrene copolymer.

A preferred composition is one in which the organic material is a synthetic organic polymer or a lubricant oil.

A composition in which the organic material is a polyolefin or an elastomer is also preferred.

The compounds of formula I will usually be blended with the material to be stabilised in an amount of 0.01 to 10 by weight, typically 0.01 to 5 by weight, preferably 0.01 to 2% by weight, based on the total amount of said material to be stabilised. It is especially preferred to use the novel compounds in amounts of 0.01 to 0.5%, most preferably of 0.05 to 0.3%.

In addition to the compounds of formula I, the novel compositions may contain conventional additives, typically those listed hereinbelow.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4'-dimethyl-6-(1'-methyundec-1'-yl)phenol, 2,4-dimethyl-6-(1'-methylheptadec-1'-yl)phenol, 2,4-dimethyl-6-(1'-methyltridec-1'-yl)phenol and mixtures therof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl4-hydroxyanisole, 3,5-di-tert-butyl-4-hydroxyanisole, 3,5-di-tert-butyl-4-hydroxyphenylstearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3, 6-di-sec-amylphenol), 4,4'-bis-(2,6-dimethyl-4-hydroxyphenyl)disulfide.

1.5. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl) pentane.

1.6. O—, N— and S-benzyl compounds, for example 3,5, 3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3, 5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3, 5-di-tert-butyl-4-hydroxybenzyl)phenol.

1.9. Triazine Compounds, for example 2,4-bis (octylmercapto)-6-(3,5-di-tert-butyl-4-hydroxyanilino)-1, 3,5-triazine, 2-octylmercapto-4,6-bis(3,5-di-tert-butyl-4-hydroxyanilino)- 1,3,5-triazine, 2-octylmercapto-4,6-bis (3,5-di-tert-butyl-4-hydroxyphenoxy)-1,3,5-triazine, 2,4, 6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl) isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.13. Esters of β-(5-tert-butyl-4-hydroxy-3-methylphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl- 1-phospha-2,6,7-trioxabicyclo[2.2.2] octane.

1.14 Esters of β-(3,5-dicyclohexyl-4-hydroxyphenyl) propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.15 Esters of 3,5-di-tert.-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

2. UV absorbers and light stabilisers 2.1.2-(2'-Hydroxyphenyl)benzotriazoles, for example 2-(2'-hydroxy-5'-methylphenyl)-benztriazole, 2-(3',5'-di-tert-butyl-2'-hydroxyphenyl)-benztriazole, 2-(5'-tert-butyl-2'-hydroxyphenyl)-benztriazole, 2-(2'-hydroxy-5'-(1,1,3,3-tetramethylbutyl)phenyl)-benztriazole, 2-(3',5'-di-tert-butyl-2'-hydroxyphenyl)-5-chlor-benztriazole, 2-(3'-tert-butyl-2'-hydroxy-5'-methylphenyl)-5-chlor-benztriazole, 2-(3'-sec-butyl-5'-tert-butyl-2'-hydroxyphenyl)-benztriazole, 2-(2'-hydroxy-4'-octoxyphenyl)-benztriazole, 2-(3',5'-di-tert-amyl-2'-hydroxyphenyl)-benztriazole, 2-(3,',5'-bis(α,α-dimethylbenzyl)-2-hydroxyphenyl)-benztriazole, mixture of 2-(3'-tert-butyl-2'-hydroxy-5'-(2-octyloxycarbonylethyl)phenyl)-5-chlor-benztriazole, 2-(3'-tert-butyl-5'-[2-(2-ethylhexyloxy)

carbonylethyl]-2'-hydroxyphenyl)-5-chlor-benztriazole, 2-(3'-tert-butyl-2'-hydroxy-5'-(2-methoxycarbonylethyl) phenyl)-5-chlor-benztriazole, 2-(3'-tert-butyl-2'-hydroxy-5'-(2-methoxycarbonylethyl)phenyl)-benztriazole, 2-(3'-tert-butyl-2'-hydroxy-5'-(2-octyloxycarbonylethyl) phenyl-benztriazole, 2-(3'-tert-butyl-5'-[2-(2-ethylhexyloxy)carbonylethyl]-2'-hydroxyphenyl)-benztriazole, 2-(3'-dodecyl-2'-hydroxy-5'-methylphenyl)-benztriazole, und 2-(3'-tert-butyl-2'hydroxy-5'-(2-isooctyloxycarbonylethyl)phenyl-benztriazole, 2,2'-methylene-bis[4-(1,1,3,3-tetramethylbutyl)-6-benztriazole-2-yl-phenol]; the transesterification product of 2-[3'-tert-butyl-5'-(2-methoxycarbonylethyl)-2'-hydroxyphenyl]-2H-benztriazole with polyethylene glycol 300; [R—CH$_2$CH$_2$—COO(CH$_2$)$_3$]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4 -dodecyloxy, 4-benzyloxy, 4,2', 4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano,-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, tdethanolarnine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4-n-butyl-amino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis (3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy) phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)- 1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis (salicyloyl)thiopropionyl dihydrazide.

4. Further phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or uidecyl esters, mercaptobenzimidazole or the zinc salt of 2-mercaptobenzimidazole, zinc dibutyldithiocarbamate, dioctadecyl disulfide, pentaerythritol tetrakis(⊖-dodecylmercapto)propionate.

6. Polyamide stabilisers, for example copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863 or U.S. Pat. No. 4,338,244, or 3-[4-(2-acetoxyethoxy)phenyl]-5,7-di-tert-butyl-benzofuran-2-one 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4 ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

Novel lubricant formulations may contain still other additives that are added to improve wear properties, typically fuerther antioxidants, metal deactivators, rust inhibitors, viscosity index improvers, pour-point depressants, dispersants/suffactants and antiwear additives. Representative examples of antioxidants will be found in item 1 of the above list. Exemplary further additives for the novel lubricant composition are:

Examples of aminic antioxidants:
N,N'-diisopropyl-p-phenylenediamine, N,N'-di-sec-butyl-p-phenylenediamine, N,N'-bis-(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-tohenesulfamoyl)diphenylamine, N,N'-dimethyl-N,N'-di-sec-butyl-p-phenylenediamine, diphenylamine, N-allyldiphenylarnine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl) sebacate, 2,2,6,6-tetramethylpiperidin-4-one and 2,2,6,6-tetramethylpiperidin-4-ol.

Examples of other antioxidants:
Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10, 14-tetrathiahexadecane.

Examples of metal deactivators, for example for copper, are:

a) Benzotriazoles and derivatives thereof, for example 4- or 5-alkylbenzotriazoles (e.g. tolutriazole) and derivatives thereof, 4,5,6,7-tetrahydrobenzouiazole and 5,5'-methylenebisbenzotriazole; Mannich bases of benzotriazole or tolutriazole, e.g. 1-[bis(2-ethylhexyl) aminomethyl)tolutriazole and 1-[bis(2-ethylhexyl) aminomethyl)benzotriazole; and alkoxyalkylbenzotriazoles such as 1-(nonyloxymethyl) benzotriazole, 1-(1-butoxyethyl)benzotriazole and 1-(1-cyclohexyloxybutyl)tolutriazole.

b) 1,2,4-Triazoles and derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles.

c) Imidazole derivatives, for example 4,4'-methylenebis(2-undecyl-5-methylimidazole) and bis[(N-methyl) imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin-2-one.

e) Amino compounds, for example salicylidenepropylenediamine, salicylaminoguanidine and salts thereof.

Examples of rust inhibitors are:

a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-(carboxyethyl)-1-dodecyl-3-methylglycerol and the amine salts thereof.

b) Nitrogen-containing compounds, for example:

I. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.

II. Heterocyclic compounds, for example: substituted imidazolines and oxazolines, and 2-heptadecenyl-1-(2-hydroxyethyl)imidazoline.

c) Phosphorus-containing compounds, for example: Amine salts of phosphoric acid partial esters or phosphonic acid partial esters, and zinc dialkyldithiophosphates.

d) Sulfur-containing compounds, for example: barium dinonylnaphthalenesulfonates, calcium petroleum sulfonates, alkylthio-substituted aliphatic carboxylie acids, esters of aliphatic 2-sulfocarboxylic acids and salts thereof.

e) Glycerol derivatives, for example: glycerol monooleate, 1-(alkylphenoxy)-3-(2-hydroxyethyl)glycerols, 1-(alkylphenoxy)-3-(2,3-dihydroxypropyl)glycerols and 2-carboxyalkyl-1,3-dialkylglycerols.

Examples of viscosity index improvers are:

Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are:

Polymethacrylate and alkylated naphthalene derivatives.

Examples of dispersants/suffactants are:

Polybutenylsuccinic amides or -imides, polybutenylphosphonic acid derivatives and basic magnesium, calcium and barium sulfonates and phenolates.

Examples of antiwear additives are:

Sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl)aminomethyltolyltriazole, derivatives of 2,5-dimercapto-1,3,4-thiadiazole, ethyl 3-[(diisopropoxyphosphinothioyl)thio]propionate, triphenyl thiophosphate (triphenylphosphorothioate), tris(alkylphenyl) phosphorothioate and mixtures thereof (for example tris (isononylphenyl) phosphorothioate), diphenyl mononoonylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris [isooctyl 2-acetate], derivatives of 2-mercaptobenzothiazole such as 1-[N,N-bis-(2-ethylhexyl)aminomethyl]-2-mercapto-1H-1,3-benzothiazole, and ethoxycarbonyl-5-octyldithiocarbamate.

The conventional additives are typically used in concentrations of 0.01 to 10%, based on the total weight of the material to be stabilised.

Some of the novel compounds of formula I are liquid and can for this reason be very readily incorporated in the materials to be stabilised. They are therefore also especially suitable for spray application. The novel compounds are immediately soluble in oils, so that heating the substrate for the dissolving process can be dispensed with. The low volatility of the novel compounds of formula I prevents migration from the polymer during processing.

The compounds of formula I and further optional additives are incorporated in the organic material by known methods. Incorporation in the materials can be effected by blending them with, or by applying thereto, the compound of formula I and further optional additives by methods which are commonly used in the art. If the organic materials are polymers, especially synthetic polymers, the incorporation can be effected before or during the fabrication of shaped articles or by applying the dissolved or dispersed compound to the polymer, with or without subsequent evaporation of the solvent. In the case of elastomers, these may also be stabilised as lattices. A further means of blending the compound of formula I into polymers consists in adding said compound before, during or directly after the polymerisation of the corresponding monomers or before crosslinking. The compound of formula I can also be added in encapsulated form (e.g. in waxes, oils or polymers). If the compound of formula I is added before or during polymerisation, it can also act as regulator for the chain length of the polymers (chain terminator).

The compounds of formula I can also be added in the form of a masterbatch which contains these compounds to the polymers to be stabilised, typically in a concentration of 2.5 to 25% by weight.

The stabilised materials may be used in any form of presentation, typically as sheets, filaments, ribbons, mouldings, profiles or binders for paints and varnishes, adhesives or putties.

The invention is illustrated in more detail by the following Examples in which, as also throughout the remainder of the description and in the claims, parts and percentages are by weight, unless otherwise indicated.

EXAMPLE 1

Preparation of a compound of formula I, wherein n=5 and 6, $R_3 = C_{12}$alkyl and $C_{13}$alkyl

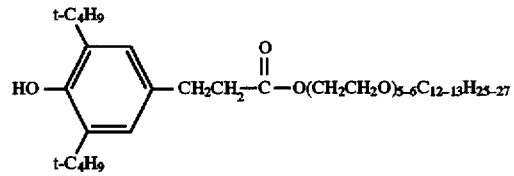

146.2 g (0.5 mol) of methyl 3-(3,5-di-tert-butyl-4-hydroxyphenyl)propionate (®Metilox, Ciba-Geigy) and 225.2 g (0.5 mol) of ®Dobanol 23-6,5* (Shell) are charged under nitrogen to a 750 ml round-bottomed flask and heated to 80° C. Then 0.23 g (2% molar) of lithium amide are added to the yellowish clear solution and the temperature is further raised. From about 120° C. methanol slowly begins to split off. After 1 hour the temperature is 165° C., and the reaction mixture is kept at this temperature for 8 hours. The resultant brown melt is cooled to room temperature, taken up in 500 ml of toluene and washed with 3×200 ml of water. The organic phase is separated, dried over sodium sulfate and filtered. The filtrate is concentrated and the residue is dried under a high vacuum at 80° C., giving 347.6 g (i.e. 97.8% of theory) of the title compound as a clear brownish oil.

Elemental analysis:

calcd: C: 69.3% H: 10.3% found: C: 69.3% H: 10.5%

*®Dobanol 23-6,5 is a mixture of primary alcohols containing a different number of ethylene oxide units and alkyl radicals having a relative molar mass of 480:

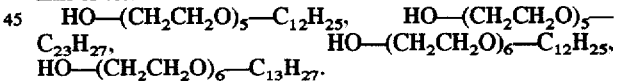

EXAMPLE 2

Preparation of a compound of formula I, wherein n=5 and 6, $R_3 = C_{12}$alkyl and $C_{13}$alkyl

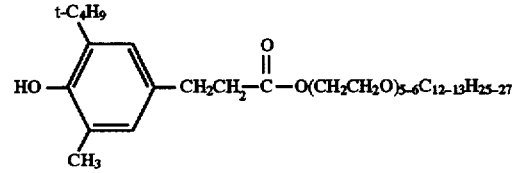

With stirring, 25.0 g (0.1 mol) of methyl 3-(3-tert-butyl-4-hydroxy-5-methylphenyl)propionate and 45.0 g (0.1 mol) of ®Dobanol 23-6,5 are heated to 80° C. in a 350 ml sulfonating flask with descending condenser and nitrogen inlet. Then 0.1 g (5% molar) of lithium amide is added to the clear yellowish melt and methanol begins to split off at c. 120° C. The temperature of the reaction mixture is raised to 165° C.

and these conditions are kept for 6 hours. After cooling to c. 80° C., 100 ml of toluene are added and the mixture is washed with 3×100 ml of water. The organic phase is separated, dried over sodium sulfate and filtered. The filtrate is concentrated on a rotary evaporator and the residue is dried for 1 hour at 80° C. under a high vacuum, giving 64.2 g (96% of theory) of a brownish oil.

Elemental analysis:

calcd: C: 68.23% H: 10.25% found: C: 68.80% H: 10.14%

EXAMPLE 3

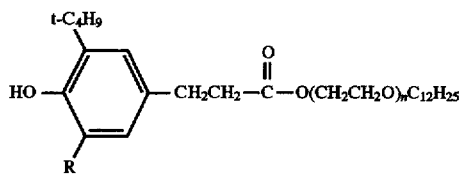

R=tert-butyl n=3

With stirring, 58.5 g (0.2 mol) of methyl 3-(3,5-di-tert-butyl-4-hydroxyphenyl)propionate and 63.7 g of ®Exxal12+3EO (polyethylene glycol sold by Exxon) are heated to c. 80° C. in a 350 ml sulfonating flask with descending condenser and nitrogen inlet. Then 0.4 g of dibutyltin oxide is added to the clear yellowish melt. Methanol begins to split off at c. 145° C. The temperature of the reaction mixture is raised to 155° C. and these conditions are kept for 12 hours. Yield: 144.4 g (99% of theory) of a brown viscous oil.

Elemental analysis:

calcd: C: 72.62% found: C: 71.85%

H: 10.80% H: 10.90%

EXAMPLES 4–6

The compounds of Examples 4–6 are prepared in general accordance with the procedure described for obtaining the compound of Example 3, using in accordance with the definition of R either methyl 3-(3,5-di-tert-butyl-4-hydroxyphenyl)propionate or methyl 3-(3-tert-butyl-4-hydroxy-5-methylphenyl)propionate and varying the reaction time as indicated in the Table. Structures and physical data of the compounds are given in Table 1.

TABLE 1

| Ex-am-ple | Batch [mol] | R | n | Reac-tion time [h] | Yield [%] | Elemental analysis [%] | | | |
|---|---|---|---|---|---|---|---|---|---|
| | | | | | | C calcd | C found | H calcd | H found |
| 4 | 0.2 | CH₃ | 3 | 12 | 86.6 | 72.62 | 71.85 | 10.80 | 10.90 |
| 5 | 0.1 | t-C₄H₉ | 8 | 5 | 99.0 | 67.63 | 67.70 | 10.34 | 10.30 |
| 6 | 0.1 | CH₃ | 8 | 4 | 93.0 | 66.63 | 66.80 | 8.79 | 8.60 |

EXAMPLE 7

Heat-ageing of polypropylene 100 parts of polypropylene (®Profax 650 I, prestabilised with 0.1% of calcium stearate) are kneaded with 0.2 part of test compound in a Brabender plastograph at 200° C. for 10 minutes. The composition so obtained is subsequently moulded in a platen press for 6 minutes at 260° C. to 1 mm sheets from which strips 1 cm wide and 17 cm long are cut. The test for the effectiveness of the additive incorporated in the test strip is carried out by heat-ageing in a circulating air oven at 135° C. and 149° C., using an additive-free strip for comparison purposes. Three strips made from each formulation are used for the test. The initial decomposition which is easily recognisable from complete embrittlement of the strip is defined as the end point. The results are expressed in days. The results are reported in the following Tables 2 and 2a.

TABLE 2

| Stabiliser | Days to the onset of de-composition at 135° C. |
|---|---|
| none | 2 |
| of Example 1 | 82 |
| of Example 2 | 48 |
| of Example 5 | 47 |

TABLE 2a

| Stabiliser | Days to the onset of de-composition at 149° C. |
|---|---|
| none | <1 |
| of Example 5 | 14 |
| of Example 6 | 12 |

EXAMPLE 8

Deposit and Oxidation Panel Test (DOPT)

The Deposit and Oxidation Panel Test is a modified version of a method of testing engine oils, especially diesel engine oils, which has been described by G. Abellaneda et al, IIIè Symposium CEC, 1989, 61, New Carendish Street, London W1M8AR, England. The object is to test the suitability of the stabilised oils to prevent deposits on the piston. The test duration is 20 hours, the panel temperature 260° C. and the oil flow is 1 ml/minute. The humid atmosphere is enriched with 260 ppm of 260 ppm NO₂ and 26 ppm of SO₂. After the test, the panel on to which the oil drips is weighed and assessed visually. The lower the figures, the better the stabiliser effect of the tested compound. Commercially available CD oil diluted with STANCO 150 base oil is used as lubricating oil. The stabiliser indicated in Table 3 is blended with this prepared oil in an amount of 0.6% by weight, based on said oil and subjected to a DOPT.

TABLE 3

| Stabiliser | Deposits on the panel | |
|---|---|---|
| | weight [mg] | visual |
| none | 72 | 9 |
| of Example 1 | 24 | 14 |

What is claimed is:

1. A compound of formula I

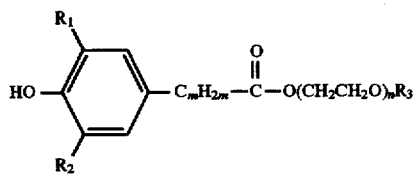

wherein $R_1$ is $C_1$–$C_{18}$alkyl, $C_5$–$C_{12}$cycloalkyl, phenyl, benzyl, α-methylbenzyl or α,α-dimethylbenzyl, $R_2$ is hydrogen or has one of the meanings given for $R_1$, $R_3$ is $C_4$–$C_{50}$alkyl, m is 1, 2 or 3, and n is a number from 1 to 15.

2. A compound of formula I according to claim 1, wherein $R_1$ is $C_1$–$C_4$alkyl.

3. A compound of formula I according to claim 1, wherein $R_3$ is $C_8$–$C_{30}$alkyl.

4. A compound of formula I according to claim 1, wherein m is 2.

5. A compound of formula I according to claim 1, wherein n is 2–12.

6. A compound of formula I according to claim 1, wherein $R_1$ and $R_2$ are identical.

7. A compound of formula I according to claim 6, wherein $R_1$ and $R_2$ are tert-butyl, $R_3$ is $C_{10}$–$C_{18}$alkyl, n is 3–8 and m is 2.

8. A mixture of compounds of formula I according to claim 1, obtainable by reacting a compound of formula IV

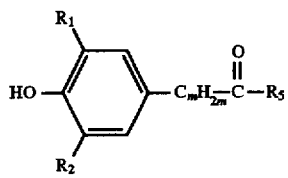

wherein $R_1$ is $C_1$–$C_{18}$alkyl, $C_5$–$C_{12}$cycloalkyl, phenyl, benzyl, α-methylbenzyl or α,α-dimethylbenzyl, $R_2$ is hydrogen or has one of the meanings given for $R_1$, m is 1, 2 or 3, and $R_5$ is OH, $C_1$–$C_4$alkoxy or Cl, with a mixture of alcohols of formula III $$R_3(OCH_2CH_2)_nOH \qquad (III)$$

wherein $R_3$ is $C_4$–$C_{50}$alkyl, and n is a number from 1–15, said mixture of alcohols comprising at least two alcohols having different values for n and/or coning different radicals $R_3$.

9. A composition comprising an organic material that is suceptible to thermal, oxidative and/or actinic degradation and at least one compound of formula I as claimed in claim 1.

10. A composition according to claim 9, wherein the organic material is a synthetic organic polymer or a lubricant oil.

11. A composition according to claim 10, wherein the organic material is a polyolefin or an elastomer.

12. A method of stabilising organic material against thermal, oxidative and/or actinic degradation, which comprises incorporating in said material at least one compound of formula I as claimed in claim 1.

13. A compound of formula I according to claim 1, wherein $R_1$ is cyclohexyl.

14. A compound of formula I according to claim 1, wherein $R_1$ is tert-butyl.

15. A compound of formula I according to claim 1, wherein $R_3$ is $C_{10}$–$C_{18}$alkyl.

16. A compound of formula I according to claim 1, wherein m is 3.

* * * * *